(12) United States Patent
Kosel et al.

(10) Patent No.: US 9,968,549 B2
(45) Date of Patent: May 15, 2018

(54) MAGNETICALLY CONTROLLED PERMEABILITY MEMBRANES

(71) Applicant: KING ABDULLAH UNIVERSITY OF SCIENCE AND TECHNOLOGY, Thuwal (SA)

(72) Inventors: Jürgen Kosel, Thuwal (SA); Niveen Khashab, Thuwal (SA); Amir Zaher, Thuwal (SA)

(73) Assignee: KING ABDULLAH UNIVERSITY OF SCIENCE AND TECHNOLOGY, Thurwal (SA)

( * ) Notice: Subject to any disclaimer, the term of this patent is extended or adjusted under 35 U.S.C. 154(b) by 1210 days.

(21) Appl. No.: 13/800,564

(22) Filed: Mar. 13, 2013

(65) Prior Publication Data

US 2013/0289516 A1  Oct. 31, 2013

Related U.S. Application Data

(60) Provisional application No. 61/614,814, filed on Mar. 23, 2012.

(51) Int. Cl.
*A61K 9/00* (2006.01)
*A61M 37/00* (2006.01)

(52) U.S. Cl.
CPC .......... *A61K 9/0009* (2013.01); *A61M 37/00* (2013.01); *A61K 9/0024* (2013.01)

(58) Field of Classification Search
CPC .. A61M 37/00; A61K 9/0009; B22F 2998/00; B22F 2001/0033; B22F 1/0025; C22C 2202/02
See application file for complete search history.

(56) References Cited

U.S. PATENT DOCUMENTS

| | | | |
|---|---|---|---|
| 7,335,526 B2* | 2/2008 | Peters | G01N 27/4146 257/414 |
| 8,424,598 B2* | 4/2013 | Roddy | C04B 40/0641 166/248 |
| 8,499,792 B2* | 8/2013 | Lee | F16K 99/0001 137/828 |
| 8,569,048 B2* | 10/2013 | Fujimoto | C12M 33/00 422/552 |
| 8,632,814 B2* | 1/2014 | Brueck | A61K 41/0052 424/489 |
| 9,186,317 B2* | 11/2015 | Smyth | A61K 9/0009 |
| 2005/0263456 A1* | 12/2005 | Cooper | A61L 2/0082 210/660 |
| 2008/0044911 A1* | 2/2008 | Bock | B82Y 5/00 436/63 |

(Continued)

OTHER PUBLICATIONS

Utilization of solid nanomaterials for drug delivery. Expert Opinion on Drug Delivery. pp. 725-735, Jul. 1, 2008.*

*Primary Examiner* — Bhisma Mehta
*Assistant Examiner* — Matthew A Engel
(74) *Attorney, Agent, or Firm* — Patent Portfolio Builders PLLC

(57) ABSTRACT

A bioactive material delivery system can include a thermoresponsive polymer membrane and nanowires distributed within the thermoresponsive polymer membrane. Magnetic activation of a thermoresponsive polymer membrane can take place via altering the magnetization or dimensions of nanowires dispersed or ordered within the membrane matrix.

10 Claims, 4 Drawing Sheets

Closed State

Open State

(56) References Cited

U.S. PATENT DOCUMENTS

| | | | |
|---|---|---|---|
| 2008/0143906 A1* | 6/2008 | Allemand | B82Y 10/00 349/43 |
| 2008/0230763 A1* | 9/2008 | Zaidi | B22F 1/0018 257/9 |
| 2008/0280069 A1* | 11/2008 | Parce | B82B 3/00 427/580 |
| 2008/0315430 A1* | 12/2008 | Weber | B82Y 10/00 257/774 |
| 2009/0258073 A1* | 10/2009 | Tishin | A61K 9/0009 424/489 |
| 2010/0112373 A1* | 5/2010 | Coffey | B32B 33/00 428/608 |
| 2010/0303722 A1* | 12/2010 | Jin | A61L 27/30 424/9.1 |
| 2011/0151586 A1* | 6/2011 | Chen | B22F 1/0062 436/531 |
| 2011/0159070 A1* | 6/2011 | Jin | A61L 27/06 424/423 |
| 2011/0298455 A1* | 12/2011 | Liang | B01L 3/502715 324/252 |
| 2012/0038356 A1* | 2/2012 | Kosel | G01R 33/0052 324/251 |
| 2013/0289516 A1* | 10/2013 | Kosel | A61K 9/0009 604/500 |
| 2013/0337034 A1* | 12/2013 | Kosel | A61K 41/0052 424/443 |
| 2014/0084913 A1* | 3/2014 | Kosel | G01R 33/072 324/252 |
| 2014/0086962 A1* | 3/2014 | Jin | A61L 31/022 424/400 |
| 2015/0117157 A1* | 4/2015 | Li | G01N 29/041 367/189 |

\* cited by examiner

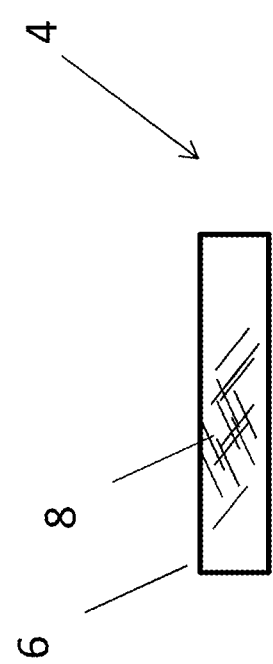

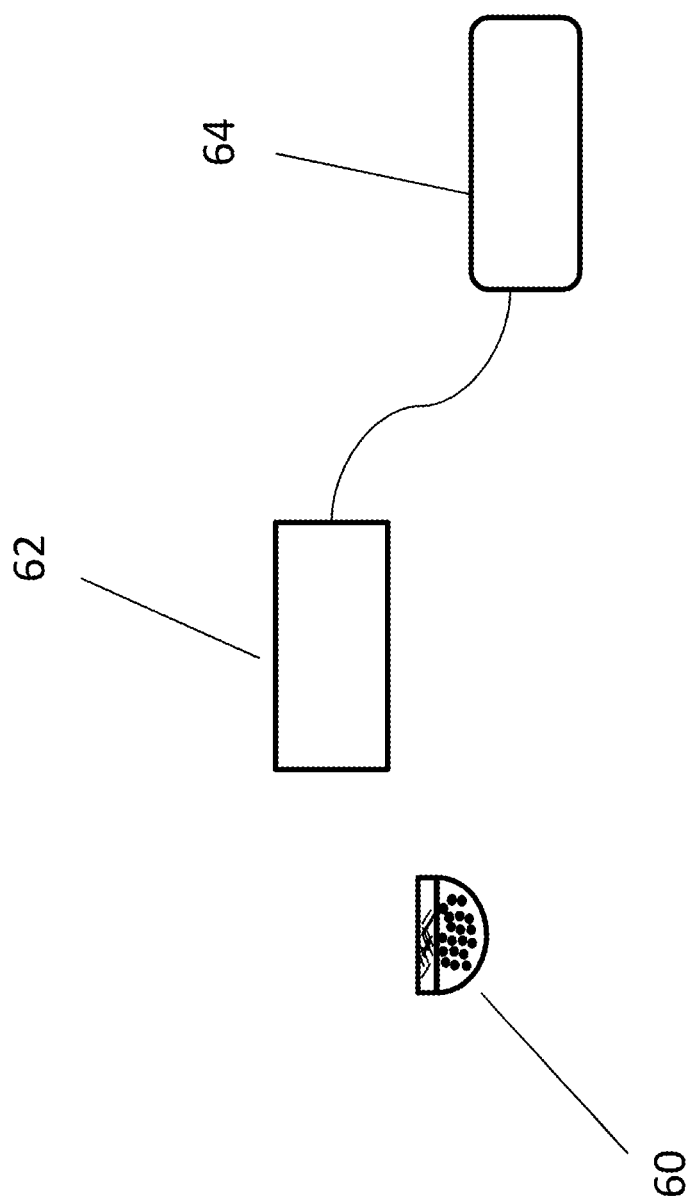

MAGNETICALLY CONTROLLED PERMEABILITY MEMBRANES

CLAIM OF PRIORITY

This application claims priority to U.S. Patent Application Ser. No. 61/614,814, filed on Mar. 23, 2012, the entire contents of which are hereby incorporated by reference.

TECHNICAL FIELD

This invention relates to magnetically controlled permeability membranes.

BACKGROUND

A major challenge in the development of advanced drug formulations involves the elaboration of delivering systems providing controlled release of bioactive materials such as drugs or biologics. In order to achieve controlled release, the bioactive materials can be embedded in a polymer matrix or in layered structure. In the latter, layer dissolution rate determines the release rate of the bioactive material. Despite significant research efforts, challenges continue to exist for controlled drug delivery.

SUMMARY

A delivery device can include a thermoresponsive polymer membrane and a plurality of magnetic nanowires distributed within the thermoresponsive polymer. The plurality of magnetic nanowires can respond to a magnetic field whereby permeability of the thermoresponsive polymer membrane is altered by exposure to a magnetic field such that a bioactive material passes through the membrane in the altered condition and not in the unaltered condition. The thermoresponsive polymer membrane can be, for example, poly(N-isopropylacrylamide) (PNIPAAm) or poly(D,L-lactic-co-glycolic acid), and any combination thereof. In another embodiment, the device includes a reservoir configured to contain the bioactive material in contact with the thermoresponsive polymer membrane. In another embodiment, the reservoir can be made of the thermoresponsive polymer membrane.

The plurality of magnetic nanowires in the thermoresponsive polymer membrane can be distributed in the membrane in a variety of different ways in order to achieve different delivery profiles. In one embodiment, the plurality of magnetic nanowires can be oriented within the thermoresponsive polymer membrane. In another embodiment, the plurality of magnetic nanowires can be randomly distributed within the thermoresponsive polymer membrane. In another embodiment, the plurality of nanowires can have a patterned distribution within the thermoresponsive polymer membrane.

In another embodiment, the plurality of magnetic nanowires can form a pattern within the thermoresponsive polymer membrane. The pattern can include a first region having a first density of nanowires and a second region having a second density of nanowires. The first density of nanowires can be higher than the second density of nanowires.

In certain embodiments, a majority or substantially all of the plurality of magnetic nanowires are magnetic. In another embodiment, at least a portion of the plurality of magnetic nanowires can be magnetostrictive.

In another aspect, a method of making a delivery device can include forming a thermoresponsive polymer membrane in contact with the plurality of magnetic nanowires, whereby permeability of the thermoresponsive polymer membrane is altered in the presence of the magnetic field such that a bioactive material passes through the membrane in the altered condition and not in the unaltered condition. In certain embodiments, forming the membrane can include mixing the thermoresponsive polymer with the plurality of nanowires and casting the membrane.

A plurality of nanowires can be grown on a substrate. The thermoresponsive polymer can be deposited on the substrate. In another embodiment, the method can include removing the substrate.

In another embodiment, the method can include cross-linking the thermoresponsive polymer. In other embodiments, the method can include contacting the thermoresponsive membrane with a reservoir configured to contain the bioactive material. The nanowires can be magnetic or magnetostrictive. In another embodiment, the thermosensitive polymer can include the reservoir.

In another embodiment, a method of delivering a bioactive material can include administering a delivery device including a thermoresponsive polymer membrane including plurality of magnetic nanowires to a patient; and applying the magnetic field to the portion of the delivery device, and releasing the bioactive material to the patient. Permeability of the thermoresponsive polymer membrane is altered in the presence of the magnetic field such that a bioactive material passes through the membrane in the altered condition and not in the unaltered condition.

In another embodiment, applying the magnetic field can include subjecting the thermoresponsive polymer membrane to a magnetic field strength effective to alter porosity to the thermoresponsive polymer membrane, wherein the thermoresponsive polymer membrane is substantial non-porous to a bioactive material prior to applying the magnetic field and the thermoresponsive polymer membrane is substantially porous to the bioactive material when the magnetic field is applied to the membrane, and passing a bioactive material through the membrane to the patient.

In another embodiment, the method can include introducing the device to the patient. In another embodiment, applying the magnetic field can increase the average pore size in the thermoresponsive polymer membrane. In another embodiment, applying the magnetic field can include generating the magnetive field inside the patient. In another embodiment, applying the magnetic field can include generating the magnetive field external to the patient.

The bioactive material can be a drug, small molecule, protein, peptide, antibody, prodrug, small molecule, vitamin, DNA, RNA, siRNA, chemotherapeutic, immunotherapeutic, or other therapeutic compound.

Other aspects, embodiments, and features will be apparent from the following description, the drawings, and the claims.

BRIEF DESCRIPTION OF THE DRAWINGS

FIG. 1 is a diagram depicting a delivery device.

FIG. 2 is a diagram depicting a delivery device including a reservoir.

FIG. 4 is a diagram depicting a system including the delivery device.

DETAILED DESCRIPTION

Figure 2B:
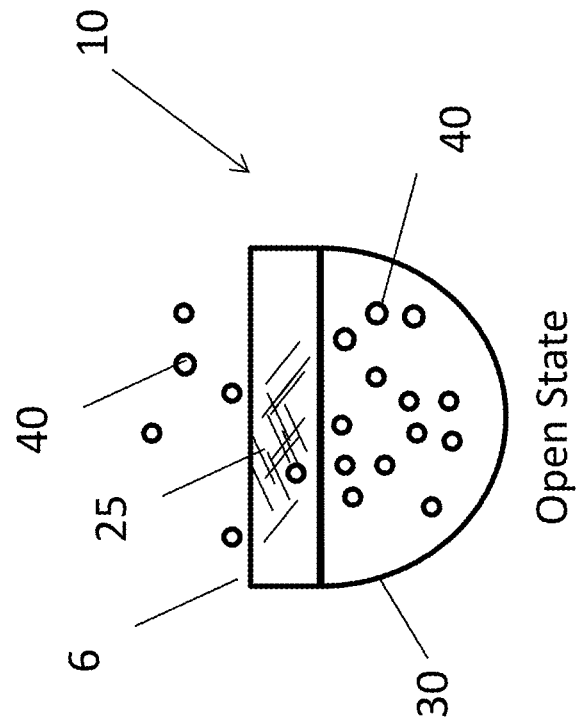
FIG. 2B is a diagram depicting the delivery device in an open state.

A delivery device for a bioactive material can include magnetic nanowires in a thermoresponsive polymer matrix, which can form a membrane that controls bioactive material delivery. The device, and methods of delivering a bioactive material, can rely on control of the permeability of the thermoresponsive polymer membrane. The nanowires can be used to adjust or alter the permeability of the thermoresponsive polymer by, for example, creating spots of local heating, which can alter the porosity of the membrane. The nanowires can create spots of local heating by applying a magnetic field. For example, magnetic activation of a thermoresponsive polymer membrane, via the actuation of magnetostrictive nanowires dispersed and ordered within the membrane matrix, can activate the membrane to change its permeability for water, thereby acting like a valve that opens (permeable) and closes (non-permeable). Magnetic activation can mean that the membrane permeability is changed remotely upon the application of a magnetic field. By altering the permeability of the thermoresponsive polymer membrane including nanowires, delivery of bioactive material through the membrane can be controlled, for example, allowing for sustained release or timed release of the bioactive material.

There are a number of ways to implement a remotely controlled membrane. For example, the remotely controlled membrane can be used to control the release of bioactive materials from an implantable delivery device. The delivery device can include the remotely controlled membrane, such as a magnetically activated membrane, a passive pump (e.g., controlled by the valves) based on osmotic pressure differences, a microfluidic channel (e.g., for drug flow control), or a biocompatible device capsule.

In general, the device operates by applying a magnetic field to actuate the nanowires. For example, the magnetic field applied to magnetostrictive nanowires cause the nanowires to extend and contract (e.g., oscillation or vibration). The magnetic field can be constant or oscillated. The vibration can cause heat generation in the polymer due to friction within the polymer matrix. The thermoresponsive membrane contracts or expands in the regions of heating, altering the permeability of the membrane. By properly designing the nanowire lengths and diameters, the resonant frequency at which each type of nanowire responds to the magnetic field can be altered, thereby allowing for selective triggering of different membranes, or different regions within the same membrane fabricated with different nanowires, within the device.

Surprisingly, the tunability of the physical properties of the nanowires makes them uniquely suited for creating controlled permeability membranes. Specifically, the application of magnetic nanowires, and their magnetostrictive properties, allow for specific activation of a thermoresponsive polymer membrane, allowing for complete control of porosity of the membrane.

The properties and structure of the thermoresponsive polymer membrane can be sensitive to a variety of physical and chemical conditions of the surrounding media. Sensitivity to a magnetic field can affect the thermoresponsive polymer membrane. In this case, magnetic activation can mean that the membrane permeability is changed remotely upon the application of a magnetic field.

Implantable delivery trigger methods that allow for remote, repeatable, and controllable bioactive material dosage delivery can greatly improve the efficiency of treatments of numerous medical conditions and can have a large impact on the biotechnology market in the near future. An ideal device for on-demand bioactive material delivery should safely contain a large quantity of bioactive material, release little or no bioactive material in the off state, be repeatedly switchable to the on state (open state) without mechanically disrupting the device, and be triggered remotely and non-invasively to release a controlled dose demanded by a patient (e.g. local pain relief) or prescribed by a doctor (e.g. localized chemotherapy). Despite the clear clinical need, few such bioactive material delivery devices have been developed so far. Most of them rely on "on-chip" power supply provided by, e.g., a battery. This increases the size of the device considerable making it unattractive for implantation. Others are limited by ineffective trigger systems and an inability to dynamically adjust bioactive material dosing. A method for triggering the osmotic pumping and release of a bioactive material can allow for remote, passive, and controlled activation via magnetic field applied by an external electromagnet.

The porosity of the membrane may be altered by changes in the membrane itself or changes in the plurality of nanowires distributed within the thermoresponsive polymer membrane. The plurality of nanowires can respond to a magnetic field whereby the average pore diameter in the thermoresponsive polymer membrane can be altered in the presence of the magnetic field such that a bioactive material passes through the pore. Magnetic activation of a thermoresponsive polymer membrane can take place via altering the dimensions or orientation of nanowires dispersed or ordered within the membrane matrix.

The thermoresponsive polymer membrane can be fabricated by mixing one or more thermoresponsive polymers in a formulation suitable to form a porous membrane. In another approach, the thermoresponsive polymer membrane can be cast polymer film, an engineered assembly of polymers, a hydrogel, or other suitable structure. The membrane covers a reservoir, for example, and impermeable polymer reservoir.

A large variety of synthetic thermoresponsive polymers with different properties, lipids, or polysaccharides can be used to form the membrane. See, for example, B. Philipp, et al., *Prog. Polym. Sci.*, 1989, 14, 91, which is incorporated by reference in its entirety. The thermoresponsive polymer membrane can include, e.g., poly(N-isopropylacrylamide) (PNIPAAm) or poly(D,L-lactic-co-glycolic acid) and any combination thereof. This provides many possibilities to tune the release properties of the thermoresponsive polymer membranes together with ensuring biocompatibility. The thermoresponsive polymer can be high molecular weight compounds or macromolecules The membrane can be reversibly permeable to low molecular weight compounds or small molecules having a molecular weight of less than 10,000 Da, preferably less than 5,000 Da and more preferably less than 1,000 Da.

A variety of different substances, such as synthetic and natural polymers, biopolymers, proteins, nucleic acids, magnetic and fluorescent inorganic nanoparticles, or lipids can be blended with the thermoresponsive polymer to form the membrane. The thickness of the membrane can depend on the conditions of its preparation. The thickness of the membrane on a substrate can be adjusted in the nanometer range, e.g. by adsorption of varying numbers of thermoresponsive polymer layers, which can give the structure semipermeable properties. See, for example, G. B. Sukhorukov, et al., *J. Phys. Chem. B* 1999, 103, 6434 and G. B. Sukhorukov, et al., *J. Microencapsulation,* 2000, 17, 2, 177-185, each of which is incorporated by reference in its entirety. The thermoresponsive polymer membrane walls can be permeable for small molecules such as small organic molecules while they exclude compounds with a higher molecular weight. See, for example, E. Donath, et al., *Nach. Chem. Tech. Lab.,* 1999, 47, 400, which is incorporated by reference in its entirety.

Activation of the membrane means changing its permeability for an active material, such as a drug, or solvent, such as water (for example, by altering the material), thereby acting like a valve that opens (permeable) and closes (non-permeable). In some circumstances, it can be desirable to provide systems having controllable or adjustable loading as well as release properties. In particular, the method can be favorable to allow the loading or release of materials into and from the thermoresponsive polymer membrane by modifying the membrane permeability. For some applications, a defined and controllable permeability of the membrane can be required in order to control the process of loading the device as well as any subsequent release under specific conditions. Due to the fact that the loading is preferably fast, but the release should be in most applications slow, it is further desired that the permeability be switchable. Therefore, it can be desirable to provide methods to influence, vary or switch properties of a membrane.

The permeability of thermoresponsive polymer membrane can be determined, varied or controlled by parameters of the membrane. The permeability to high molecular weight compounds as well as low molecular weight compounds can be adjusted according to the needs in different applications. The permeability control can offer a unique tool for entrapping molecules within the device and releasing them in a predetermined manner, e.g. over an extended period of time or at a desired, predetermined site or time point.

The method permits a reversible alteration of the permeability of membranes. This enables specifically charging the device with desired active substances or specifically releasing active substances entrapped in the device, respectively, by applying a magnetic field. For example, a permeability increase can make it possible to later charge the finished device with active substances in an "open condition." After the device has been loaded with active material, for example, during storage or transport or another time when the device is not intended to release the active substance, the permeability of the membrane to the entrapped active substance can be reduced by adjusting of suitable conditions so that no active substance can leave the device. Such a "closed condition" of the membrane prevents possibly undesired substances from entering the device. At the desired time and site of release, respectively, the active agent can be released in a defined way, for example, delayed delivery, pulsed delivery or other periodic delivery, by increasing the permeability of the membrane. In this way, it is possible to release materials from the device only after the device has been placed in position for a predetermined amount of time prior to a targeted time for delivery in certain areas of an organism. The increase in permeability can be simply induced by applying magnetic field to the membrane.

As an alternative to altering permeability of the membrane to the active material, the permeability of the membrane to solvent, or water, can be altered. When in the higher permeability state, the solvent can pass into the device and can dissolve the active material, causing it to be released from the device.

The nanowires can be magnetic in that the nanowires can change directions or orientation of their magnetization in response to a magnetic field. At least a portion of the plurality of nanowires can be magnetostrictive. The nanowires can be magnetostrictive in that the nanowires can change length in response to a magnetic field. See, for example, WO 2011/138676, which is incorporated by reference in its entirety.

Nanowires generally include at least one substantially crystalline or amorphous material. In certain embodiments, the nanostructure can include a core of a first material and at least one shell of a second (or third etc.) material, where the different material types are distributed radially about the long axis of a nanowire, a long axis of an arm of a branched nanowire, or the center of a nanocrystal, for example. Depending on the application and other design parameters, nanowires can have an aspect ratio (length-to-width ratio) of, for example, 1, 5, 10, 100, 250, 500, 800, 1000 or higher. Nanowires structures with a diameter in the range of approximately 5 nm to approximately 200 nm, with lengths in the range of approximately 10 nm to approximately 100 µm, can be formed.

Nanowires can be produced by electrodeposition, chemical etching, vapor-liquid-solid (VLS) synthesis or solution-phase synthesis, to name a few examples.

The nanowire can be substantially crystalline or amorphous.

Nanowires can have various cross-sectional shapes, including, but not limited, to circular, square, rectangular and hexagonal. In each case, the term "diameter" is intended to refer to the effective diameter, as defined by the average of the major and minor axis of the cross-section of the structure. Magnetic nanowires can be made of pure metals including rare earth metals or alloys, consisting of, e.g., cobalt, nickel, iron, gallium, terbium, dysprosium and combinations thereof. The use of different metals or of alloys allows for the tailoring of the magnetic responses under applied magnetic fields for a given region of thermoresponsive polymer.

By characterizing a dose delivery and magnetic field relationship for different nanowire and thermoresponsive polymer structures, in addition to characterization of nanowires for various shape and magnetic alloys compositions, design of the controlled permeability membranes can be optimized for specific applications, including treatment of specific diseases and physiologic conditions. For example, the magnetic field may be applied either internal or external to the patient. If external, the magnetic field must still be near enough to the patient to alter the porosity of the thermoresponsive polymer membrane. The design flexibility can allow for a precise dose-control mechanism for implantable bioactive material delivery systems to be developed which can be used to treat pain, cancer, diabetes, or Alzheimer's, as well as other conditions. The device can be produced with low cost materials with relatively small device sizes and significantly improved dose control. The membrane is controlled like an on/off switch, with no appreciable leakage through the membrane.

FIG. 1 depicts a delivery device 4 including a thermoresponsive polymer membrane 6 and a plurality of nanowires 8. The nanowires 8 can be randomly distributed in the membrane. The plurality of nanowires can be randomly distributed within the thermoresponsive polymer membrane. The plurality of nanowires can be in a patterned distribution within the thermoresponsive polymer membrane. The plurality of nanowires can form a pattern within the thermoresponsive polymer membrane. When the magnetic field is applied to the membrane, the pattern of the plurality of nanowires can cause a change in porosity only in the area of the thermoresponsive polymer membrane wherein the pattern is located. The pattern can include a region having a density of nanowires that is different from another region having a density of nanowires. One region of the thermoresponsive polymer membrane can have a higher density of nanowires than a different region that has a lower density of nanowires.

Figure 2A:
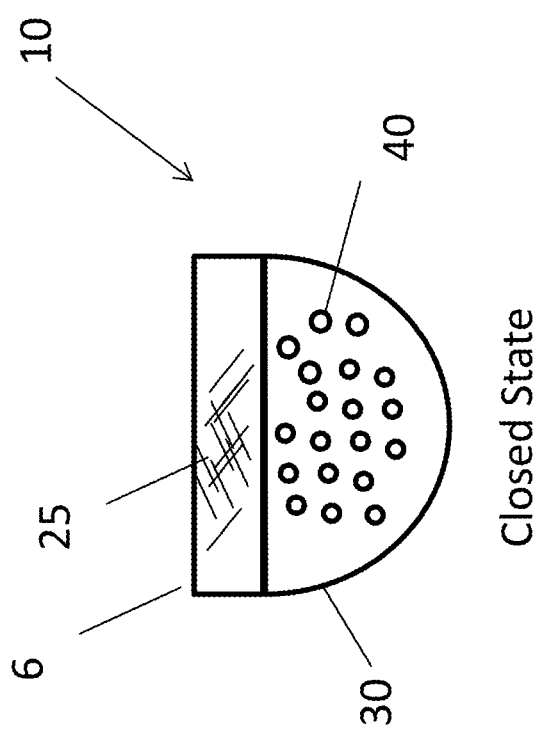
FIG. 2A is a diagram depicting the delivery device in a closed state.

Referring to FIG. 2A and FIG. 2B, a device 10 can be in a closed state (FIG. 2A) or an open state (FIG. 2B). Device 10 includes polymer membrane 6, which contains nanowires 25. Polymer membrane 6 covers reservoir 30, which contains bioactive material 40. In the closed state, the permeability of polymer membrane 6 confines bioactive material 40 to the reservoir 30. Application of a magnetic field causes the permeability of polymer membrane 6 to change, rendering it more permeable. As shown in FIG. 2B, the change in permeability permits bioactive material 40 to be released from device 10. The plurality of nanowires can be oriented substantially parallel to a surface of the thermoresponsive polymer membrane, or substantially perpendicular to the thickness of the membrane.

Figure 3:
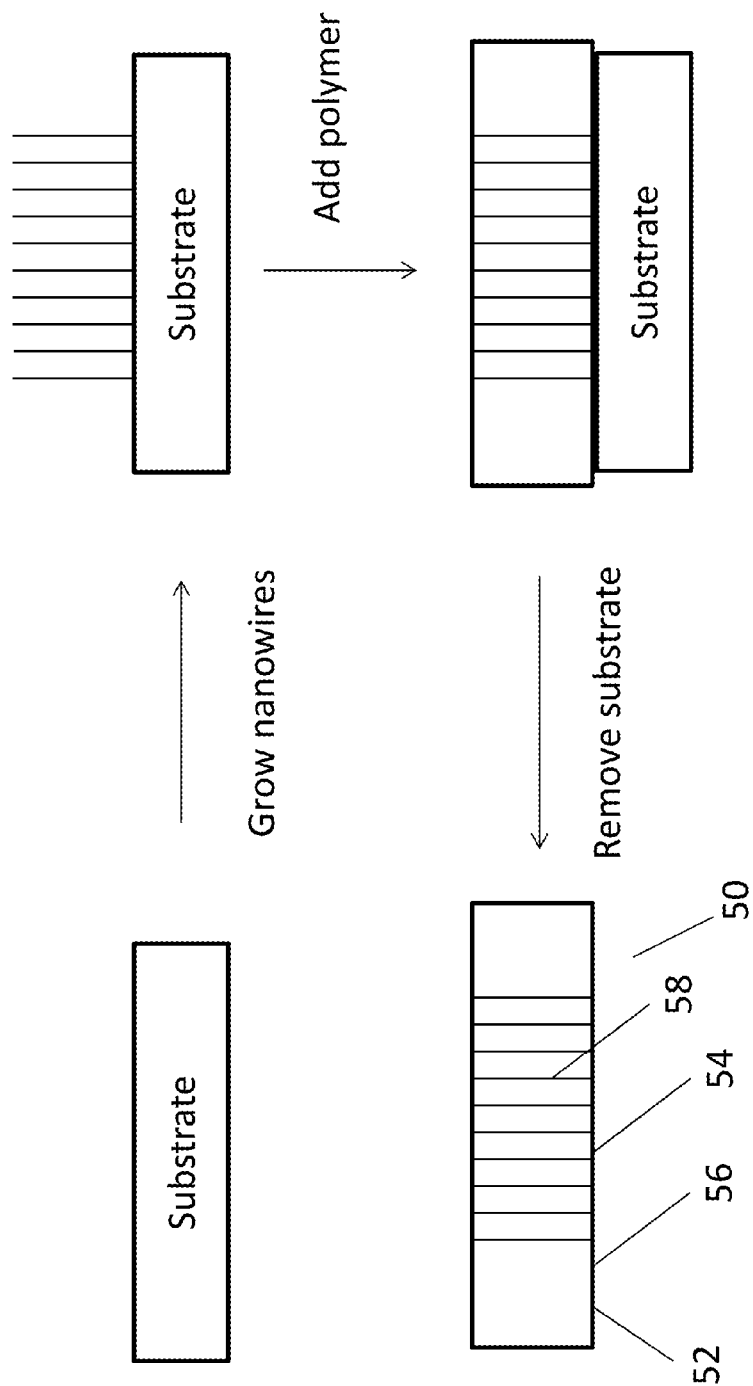
FIG. 3 is a diagram depicting a method of making the delivery device.

In FIG. 3, device 50 includes thermoresponsive polymer 52 having a plurality of nanowires 54 distributed in a regular manner in the polymer such that there is nanowire depleted region 56 and nanowire rich region 58. As such, the density of nanowires in one region can be higher than another density of nanowires. In certain circumstances, the composition, length, or diameter of the nanowires (or combinations thereof) can differ as well. The difference in nanowire density can lead to the area including the higher density pattern to have more increased porosity while the area that including the smaller density of nanowires has less porosity than the higher density region. The higher the density of wires in a region, the larger the thermoresponsive changes during magnetic activation, since there are more sources of heat from the additional wires when compared to lower densities.

In a preferred embodiment, the thermoresponsive polymer membrane may be magnetically activated via the actuation of magnetic nanowires dispersed within the membrane matrix. In this context, activation of the membrane includes changing its permeability for water, thereby acting like a valve that can change the membrane or shell to an open state (permeable) or a closed state (non-permeable). Magnetic activation can include that the membrane permeability is changed remotely upon the application of a magnetic field.

There are numerous applications for such a remotely triggered membrane. For example, a magnetic field may be applied to the membrane shell to control the release of bioactive material with an implantable bioactive material delivery device. The bioactive material delivery device can rely on several components. These components can include a remotely triggered valve composed of the magnetically activated membrane, a passive pump which is controlled by the valves, with a working principle based on, e.g., osmotic pressure differences, microfluidic channels, which may be useful for bioactive material flow control, and a biocompatible device capsule.

By applying a magnetic field, an extension and contraction of the magnetic or magnetostrictive nanowires, or a vibration, can be generated, causing heat generation due to friction within the thermoresponsive polymer matrix during oscillation. Alternatively, the change in magnetization of the magnetic nanowires can cause losses, which generate heat. In other embodiments, a combination of the two effects may apply. The membrane contracts in the regions of heating, rendering it porous and hence permeable (open state). By properly designing the nanowire lengths and diameters, the resonant frequency at which each type of nanowire responds can be controlled, thus enabling selective triggering of different membranes, and different regions within the same membrane fabricated with differing nanowires, within the device.

This method for controlling the permeability of a membrane can allow for the triggering of, e.g., an osmotic pump, which relies on the surrounding body fluid to begin pumping. The end result is a passive remotely triggered pumping mechanism for the device, made possible solely by the remote magnetic triggering.

In a preferred embodiment, magnetic nanowires can be applied specifically for achieving the activation of a thermoresponsive polymer membrane, allowing for complete control of porosity of the membrane. Previous work has relied on the heat generation created using magnetic single domain particles and the constant reversal of particle domain to control membrane porosity. See, for example, Sanrini, J. T. Jr, et al. *Angew. Chem. Int. Ed.* 39; 2396-2407, 2000 and T. Hoare, et al., *Nano Lett.*, Vol. 9, No. 10, 2009, each of which is incorporated by reference in its entirety. It is well-known magnetostrictive effect that a magnetic field has on magnetic nanowires. See, for example, P. D. McGary and B. J. H. Stadler, *J. Appl. Phys.* 97, 10R503 2005, which has been incorporated by reference in its entirety. Furthermore, thermally responsive thermoresponsive polymers, such as poly(N-isopropylacrylamide)-based nanogels have been shown to work and suggested for drug delivery application. See, for example, R. Langer, D. S. Kohane, et al., *Nano Lett.*, Vol. 9, No. 10, 2009. An advantage of using nanowires instead of particles is the ability to control the number, composition, pattern or distribution of the nanowires in the membrane. This can be a critical improvement providing predictable and repeatable results. Another advantage can include the higher heat losses than can be produced by nanowires compared to magnetic particles. Another advantage is the use of wires of different resonant frequencies, which allows activating membranes individually. Heat generation using nanowires can be used to achieve bioactive material delivery control within such a thermoresponsive polymer. Furthermore, the membrane can be used as a trigger for the osmotic pump.

In a preferred embodiment, a bioactive material delivery system including a thermoresponsive polymeric membrane embedded with nanowires can be stimulated by an external electromagnet. Stimulation of the nanowires by the electromagnet generates heat, which causes temperature dependant motion control of the membrane by the nanowires. Heat generated from stimulating (from an external source) nanowires to control the porosity and permeability of a membrane in a manner that enables the membrane to act as an on/off switch for a bioactive material delivery system or device. The system can provide more precise dose control for implantable bioactive material delivery systems by enabling the membrane to behave as a valve to control flow bioactive materials through the membrane.

One approach to make the bioactive material delivery device can include forming a thermoresponsive polymer membrane in contact with the plurality of nanowires. First, a plurality of nanowires that are responsive to a magnetic field can be grown on a substrate. The plurality of nanowires can be grown to select diameters, length or in specific patterns. See FIG. 3. Thermoresponsive polymers may then be added to cover the nanowires. Then, the substrate can be removed. See FIG. 3. Another approach to making the bioactive material delivery device includes mixing a plurality of nanowires with a thermoresponsive polymer to form a mixture and depositing the mixture to form a membrane. See FIG. 3. In certain circumstances, the thermoresponsive polymer of the membrane can be cross-linked.

As shown in FIG. 4, a system for delivery of a bioactive material to a subject in need of thee bioactive material includes device 60, magnetic activator 62, and a controller 64. Controller 64 is configured to regulate delivery of the bioactive material by switching the magnetic activator 62 on or off. The device 60 is implanted into the subject, optimally near the location in need of the bioactive material. The bioactive material can be a drug to be given to a patient by first administering the bioactive material delivery device including a thermoresponsive polymer membrane including plurality of nanowires to the patient, applying a magnetic field to a portion of the bioactive material delivery device, and releasing the bioactive material to the patient. The magnetic field can be adjusted to a field strength effective to alter porosity to the thermoresponsive polymer membrane, wherein the thermoresponsive polymer membrane is substantial non-porous to a bioactive material prior to applying the magnetic field and the thermoresponsive polymer membrane is substantially porous to the bioactive material when the magnetic field is applied to the membrane. The magnetic field can be generated inside the patient or external to the patient. If the magnetic field is external to the patient, it still must be near enough to exert alter the permeability of the thermoresponsive polymer membrane. When the magnetic field is applied, the bioactive material can pass through the membrane to the patient. For example, applying the magnetic field can increase the average pore size in the thermoresponsive polymer membrane. Magnetic field strengths for switching typically are in the µT to mT range, at frequencies ranging from some 10 Hz to about 1 MHz. Amplitudes and frequencies can strongly depend on membrane dimensions, nanowire material, design and density, as well as, in the case of multiple membranes for separate bioactive materials, the discrimination between these materials during drug release.

The size of a device employing this system can be between 50 microns and 100 mm. For example, the device can have dimensions of between 2 and 50 mm, 4 and 25 mm, for example, 5 mm, 8 mm, 10 mm, 12 mm, 15 mm, or 20 mm. The amount of bioactive material that can be loaded into the device can be limited by the size. A primary benefit of this system is a significant improvement in dose control as compared to other devices. Other benefits include improved biocompatibility and its smaller size, which makes for a more suitable implantable device. Bioactive materials with very high potency can be preferred for the device due the fact that the smaller size of the device can limit the bioactive material load and that the bioactive material can be delivered at the exact location where it is needed.

In one embodiment, deployment of the device is ideally intended to be months to years. The device can be surgically removed after deployment. The nanowires are not bioresorbable, but can be capable of migrating from the treatment site and to and through the appropriate tissues to be expelled along with a patient's digestive waste, based on the size of the nanowires.

This device potentially has broad bioactive material delivery applications including pain management, cancer, diabetes, or Alzheimer's. The magnetic or magnetostrictive properties of nanowires or the characteristics of specific thermoresponsive polymeric gels can be used for bioactive material delivery.

Other embodiments are within the scope of the following claims.

What is claimed is:

1. A delivery device comprising:
   a reservoir that contains a bioactive material to be delivered to a patient;
   a thermoresponsive polymer membrane covering the reservoir; and
   a plurality of magnetic nanowires distributed within the thermoresponsive polymer membrane,
   wherein the plurality of magnetic nanowires responds to a magnetic field whereby a permeability of the thermoresponsive polymer membrane is altered in a presence of the magnetic field such that the bioactive material is released from the reservoir by passing through the plurality of magnetic nanowires and the thermoresponsive polymer membrane in an altered condition and not in an unaltered condition.

2. The device of claim 1, wherein the thermoresponsive polymer membrane is-made of poly(N-isopropylacrylamide) (PNIPAAm), poly(D,L-lactic-co-glycolic acid) or any combination thereof.

3. The device of claim 1, wherein the reservoir is configured to contain the bioactive material in contact with the thermoresponsive polymer membrane.

4. The device of claim 1, wherein the reservoir is configured to contain the bioactive material.

5. The device of claim 1, wherein the plurality of nanowires are oriented within the thermoresponsive polymer membrane.

6. The device of claim 1, wherein the plurality of nanowires are randomly distributed within the thermoresponsive polymer membrane.

7. The device of claim 1, wherein the plurality of nanowires form a pattern within the thermoresponsive polymer membrane.

8. The device of claim 7, wherein the pattern includes a first region having a first density of nanowires and a second region having a second density of nanowires, the first density of nanowires being higher than the second density of nanowires.

9. The device of claim 1, wherein at least a portion of the plurality of nanowires are magnetic.

10. The device of claim 1, wherein the plurality of nanowires have a patterned distribution within the thermoresponsive polymer membrane.

* * * * *